United States Patent [19]

Kosasky

[11] Patent Number: 5,640,968
[45] Date of Patent: Jun. 24, 1997

[54] INSTRUMENT FOR MEASURING SALIVA VISCOELASTICITY TO DETERMINE FEMALE OVULATION TIME

[76] Inventor: Harold J. Kosasky, 25 Boylston St., Chestnut Hill, Mass. 02167

[21] Appl. No.: 524,741

[22] Filed: Sep. 7, 1995

[51] Int. Cl.$^6$ .................................................. A61B 10/00
[52] U.S. Cl. ............................................................ 128/738
[58] Field of Search ................................... 128/630, 738, 128/760; 73/54.19, 54.22

[56] References Cited

U.S. PATENT DOCUMENTS

| | | | |
|---|---|---|---|
| 3,982,423 | 9/1976 | Schuster | 73/54 |
| 4,002,056 | 1/1977 | Kopito et al. | 73/53 |
| 4,013,066 | 3/1977 | Schuster | 128/738 |
| 4,027,516 | 6/1977 | Ochodnicky et al. | 73/54.18 |
| 4,072,045 | 2/1978 | Kopito | 73/54 |
| 4,237,725 | 12/1980 | Kopito et al. | 73/54.22 |
| 4,628,941 | 12/1986 | Kosasky | 128/759 |
| 4,779,627 | 10/1988 | Kosasky | 128/738 |
| 5,086,780 | 2/1992 | Schmitt | 128/760 |

OTHER PUBLICATIONS

Gerald Oster et al., "Cyclic Variation of Sialic Acid Content in Saliva", *American Journal of Obstetrics and Gynocology*, vol. 114, No. 2, Sep. 15, 1972, pp. 190–193.

L. E. Kapito et al., "The Tackiness Rheometer Determination of the Viscoelasticity of Cervial Mucus", *Human Ovulation*, Elsevier/North–Holland Biomedical Press, 1979, pp. 351–361.

*Primary Examiner*—Sam Rimell
*Assistant Examiner*—Pamela Wingood
*Attorney, Agent, or Firm*—Morse, Altman & Benson

[57] ABSTRACT

A device for determining the timing of female ovulation by measuring the viscoelasticity of saliva, the device comprising: (a) an elongated sheath with a length along an axis and an opening at one end; (b) a reciprocable escapement with a pair of elongated arms, at least one of the arms being approximately parallel to the axis, the arms having inner extremities within the sheath remote from the opening and outer extremities in the vicinity of the opening; (c) the outer extremities having mating surfaces; (d) the escapement including a spring bias urging the separation of the mating surfaces from each other; (e) the arms being mounted for relative movement of the mating surfaces among first relational positions at which the mating surfaces are separated, second relational positions at which the mating surfaces are in contact, and third relational positions at which the mating surfaces are free to separate under the spring bias; (f) a control operatively connected to the escapement for placing the mating surfaces into the first relational positions, the second relational positions, and the third relational positions; (g) at least one of the mating surfaces being free to collect the saliva when they are in the first relational positions; (h) the mating surfaces compressing the saliva therebetween when they are in the second relational positions; (i) and a timer for measuring the time elapsed for separation of the surfaces when they are in the third relational positions.

26 Claims, 15 Drawing Sheets

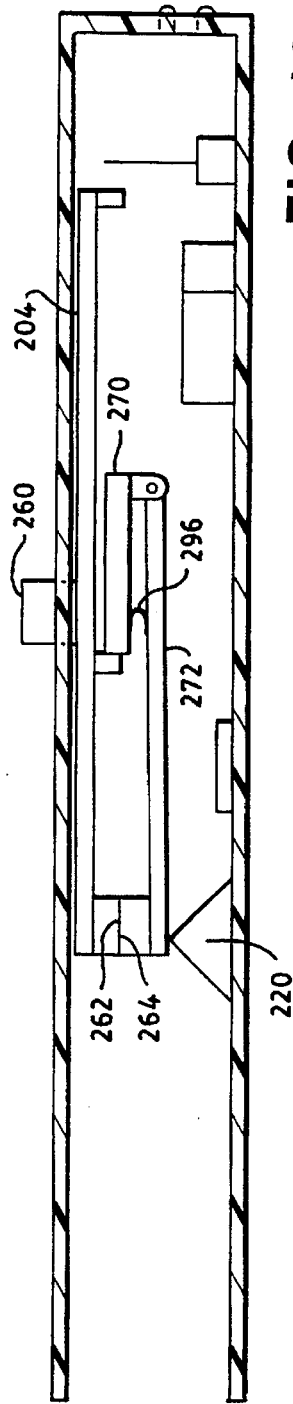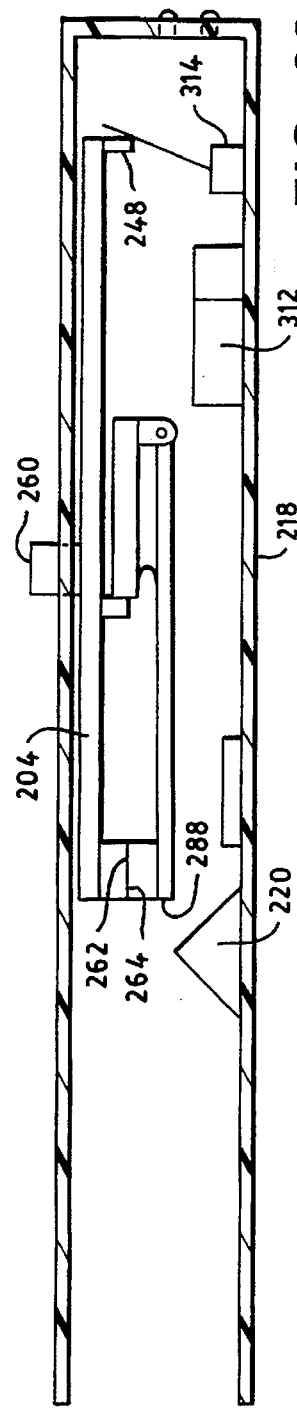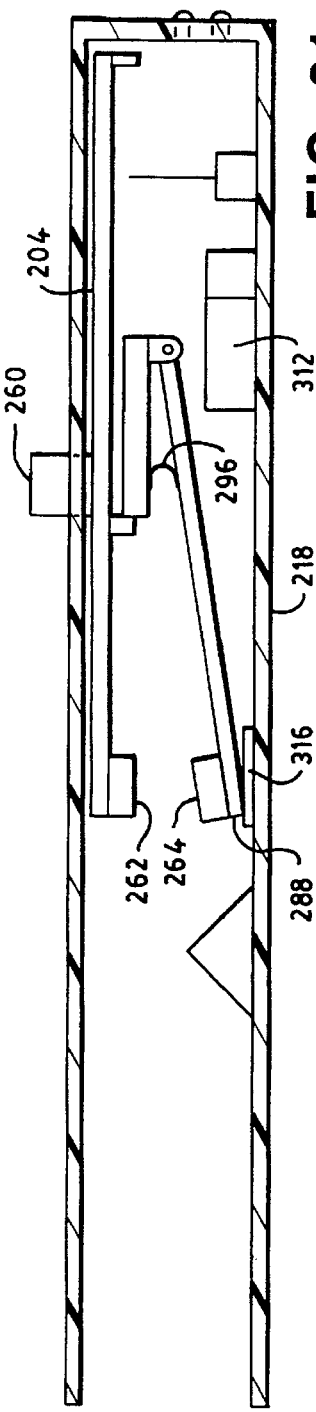

INSTRUMENT FOR MEASURING SALIVA VISCOELASTICITY TO DETERMINE FEMALE OVULATION TIME

GOVERNMENT FUNDING

The research involved in this application was funded in part by the National Institutes for Health, grant number 1 R41 HD32218-01. The intellectual property rights of the applicant and the government of the United States of America are governed by Title 37 Code of Federal Regulations Part 401.

BACKGROUND OF THE INVENTION

1. Field of the Invention

The present invention relates to the measurement of the viscoelasticity of saliva, and more particularly, to a device for the measurement of saliva viscoelasticity in order to determine a woman's ovulation time.

2. The Prior Art

It has been known that the cervical mucus of a female has a maximum fluidity just before ovulation, where ovulation is defined as the moment that an ovum is released from the follicle. This knowledge lead to the applicant's previous activities in the development of techniques for monitoring the viscoelasticity, or tackiness, and other properties of cervical mucus as a predictor of time of ovulation and to improvements in rheometer or viscometer apparatus for measuring such viscoelastic properties. See, for example, L. E. Kopita and H. J. Kosasky, "The Tackiness Rheometer Determination of the Viscoelasticity of Cervical Mucus," *Human Ovulation*, edited by E. S. E. Hafez, Elsevier, North-Holland Biomedical Press, 1979, pp. 351 et seq., and U.S. Pat. Nos. 4,002,056 and 4,167,110. Though the viscoelasticity of the cervical mucus has several small dips in its characteristic curve of viscosity versus time preceding, during, and following ovulation (a four-day period), there is a distinct identifiable minimum viscoelasticity. Instruments designed to measure this effect are described in, for example, U.S. Pat. Nos. 4,002,056 and 4,072,045.

Saliva is now known to undergo chemical changes during the menstrual cycle, including a change in its viscoelasticity. Especially pronounced is the change in viscoelasticity of sublingual saliva, the saliva found under the tongue. See, for example, S. S. Davis, "Saliva is Viscoelastic", Experientia, 26:1298, (1970), and R. H. Davis et al., "Saliva Viscosity Reflects the Time of Ovulation", Experientia, 30:911, (1974). As described in U.S. Pat. No. 4,779,627, issued on Oct. 25, 1988 to the present applicant, and entitled PROCESS AND APPARATUS FOR DETERMINING FEMALE OVULATION TIME BY MEASUREMENT OF SALIVA VISCOELASTICITY, incorporated herein by reference, the applicant previously discovered that sublingual saliva has a unique and reliably measurable minimum in viscoelasticity that is coincident with the ovulation cycle and its surge of estradiol.

There are devices on the market for measuring viscoelasticity to determine ovulation time, but these devices are designed to use cervical mucus as a sample medium, rather than saliva. The viscoelasticity of cervical mucus is an order of magnitude higher than that of saliva. So, devices designed to use cervical mucus as a sample medium are typically not sensitive enough to use saliva as a sample.

The above-identified U.S. Pat. No. 4,779,627, in addition to disclosing a process for determining female ovulation time by measuring saliva viscoelasticity, discloses a device for measuring the viscoelasticity of the sublingual saliva. The device has a shape somewhat like a syringe, with an outer cup, an inner cup concentric with and located within the outer cup, and a plunger. A roughened surface on the end of the plunger holds the saliva sample. The plunger is inserted into the inner cup until the saliva sample is compressed against the bottom of the inner cup. A predetermined amount of weight pulls the inner cup downward, stretching the saliva sample. If the viscoelasticity of the saliva is low, the saliva sample will fracture, causing the inner cup to fall to the bottom of the outer cup. An indicator at the bottom of the outer cup indicates that the inner cup has fallen to the bottom which, in turn, indicates that ovulation will soon take place. If, however, the viscoelasticity of the saliva is high, the saliva sample will hold the plunger and inner cup together so that the inner cup will not fall to the bottom, indicating that ovulation will not take place in the near future.

This device has several disadvantages. One is that the device can only be used conveniently for one person. The amount of weight that pulls the inner cup downward is selected for a specific person. There must have been a sublingual saliva sample measured from the same person at a time when the sublingual saliva is know to have the minimum viscoelasticity in order to select the amount of weight.

A second disadvantage is that the device must be taken apart in order to take a sample. The plunger must be removed from the inner cup before being inserted in the mouth to obtain a saliva sample. This has the potential for the person to easily contaminate the saliva sample by incorrectly reinserting the plunger after taking the sample, invalidating the measurement.

Thus, there continues to be a need for a device for measuring the viscoelasticity of saliva to determine a female's ovulation time that is easy to use, does not have to be calibrated for an individual, and has a low chance of sample contamination.

SUMMARY OF THE INVENTION

The object of the ovulation measuring device of the present invention is to overcome the disadvantages inherent in the devices of the prior art. The device of the present invention includes: (a) an elongated sheath having a length along an axis and an opening at one extremity; (b) a reciprocable escapement including a pair of elongated arms, at least one of the arms being disposed approximately parallel to the axis, the arms having inner extremities within the sheath remote from the opening and outer extremities in the vicinity of the opening; (c) the outer extremities having mating surfaces; (d) the escapement including a spring bias urging the separation of the mating surfaces from each other; (e) the arms being mounted for relative movement of the mating surfaces among first relational positions at which the mating surfaces are separated, second relational positions at which the mating surfaces are in contact, and third relational positions at which the mating surfaces are free to separate under the spring bias; (f) a control operatively connected to the escapement for optionally placing the mating surfaces into the first relational positions, the second relational positions, and the third relational positions; (g) at least one of the mating surfaces being free to collect the saliva when the mating surfaces are in the first relational positions; (h) the mating surfaces being constrained to compress the saliva therebetween when the mating surfaces are in the second relational positions; and (i) a timer for measuring the time elapsed for separation of the surfaces when the surfaces are in the third relational positions.

There are two preferred embodiments of the present invention. In the first embodiment, the sheath is tubular with an open top and a closed bottom. The opening in the sheath narrows into a throat. The escapement is U-shaped and is composed of a plastic or composite. The mating surfaces are at the ends of the escapement arms and the cross-piece of the escapement acts as the spring bias. Near the center of the arms are protrusions. A knob in the sheath wall allows the user to move the escapement axially into the sheath. As the protrusions pass into the throat of the sheath, the mating surfaces are forced together, and as the protrusions pass beyond the throat, the saliva holds the mating surfaces together against the spring bias until the spring bias overcomes viscoelasticity of the saliva, causing the mating surfaces to separate. The amount of time it takes for separation is measured by an electronic timer and the result is indicated by a pair of light-emitting diodes (LEDs).

In the second embodiment, the sheath is an elongated hollow rectangle with an open front, a closed rear, and a longitudinal axis. A wedge rising from the floor inside the sheath creates a throat within the sheath. The escapement includes an upper portion and a lower portion. The mating surfaces are at the outer ends of the upper and lower portions. The upper portion is substantially parallel to the longitudinal axis. The lower portion is pivotally mounted relative to the upper portion and the mating surfaces are biased apart by a spring attached to the lower portion. A knob in the sheath wall allows the user to move the upper portion axially within the sheath. As the lower portion passes over the wedge, the mating surfaces are forced together, and as the lower portion passes beyond the wedge, the saliva holds the mating surfaces together against the spring bias until the spring bias overcomes viscoelasticity of the saliva, causing the mating surfaces to separate. The amount of time it takes for separation is measured by an electronic timer and the result is indicated by a pair of LEDs.

One object of the present invention is to overcome the necessity to calibrate the device to an individual. Because the present invention relies on time as a measurement, rather than a calibrated weight, it does not have to be calibrated for an individual.

A further object of the present invention is to reduce the possibility of contamination of the saliva sample prior to measurement. The device of the present invention is completely assembled prior to the taking of the saliva sample, rather than having to be assembled after the sample is taken, thus significantly reducing the possibility of contamination of the sample.

Other objects of the present invention will in part be obvious and will in part appear hereinafter.

BRIEF DESCRIPTION OF THE DRAWINGS

For a fuller understanding of the nature and object of the present invention, reference is made to the accompanying drawings, wherein:

FIG. 19 is a cross-sectional view of the third step of operation of the embodiment of FIG. 13;

FIG. 20 is a cross-sectional view of the fourth step of operation of the embodiment of FIG. 13;

FIG. 21 is a cross-sectional view of the fifth step of operation of the embodiment of FIG. 13;

DETAILED DESCRIPTION

The present invention has two preferred embodiments, each with various configurations. The first preferred embodiment uses two prongs to take a saliva sample and the second preferred embodiment uses one prong to take a saliva sample.

Dual-Prong Embodiment

Figure 1:
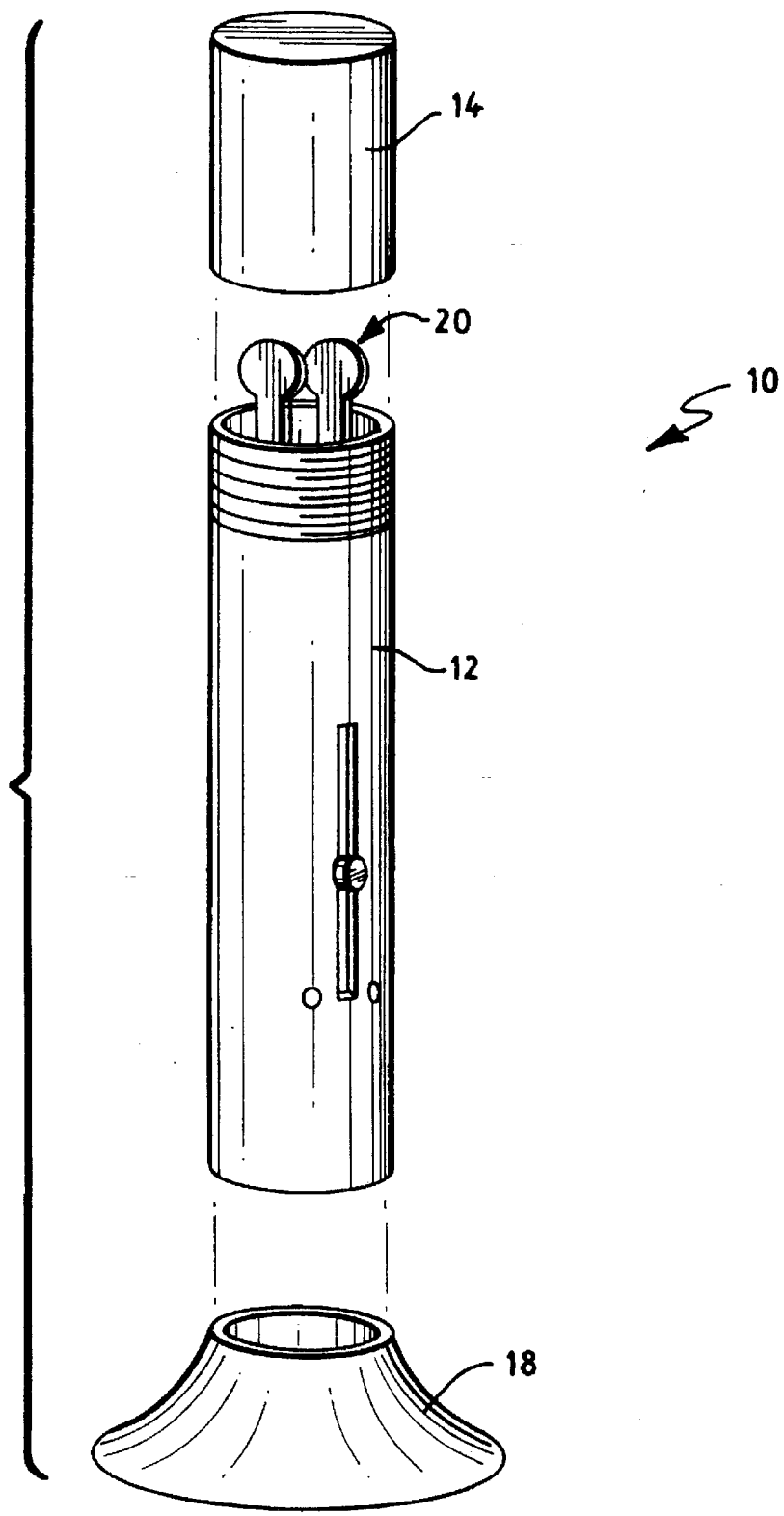
FIG. 1 is a perspective view of a dual-prong embodiment of the present invention.

FIG. 1 shows the dual-prong embodiment of the present invention 10. It is comprised of four separate components: the sheath 12, the cap 14, the stand 18, and the escapement 20.

Figure 2:
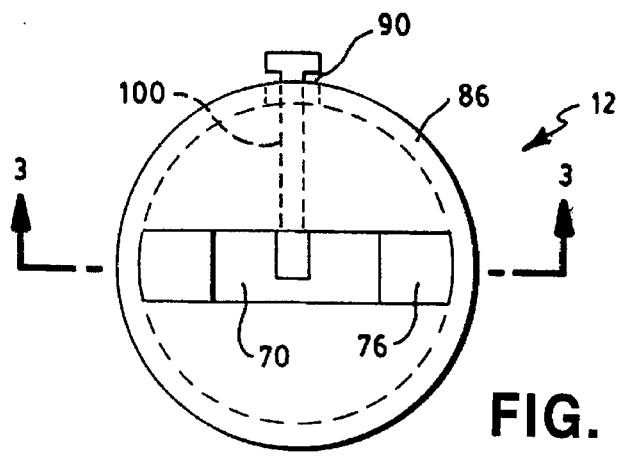
FIG. 2 is a top view of the sheath of FIG. 1.
Figure 3:
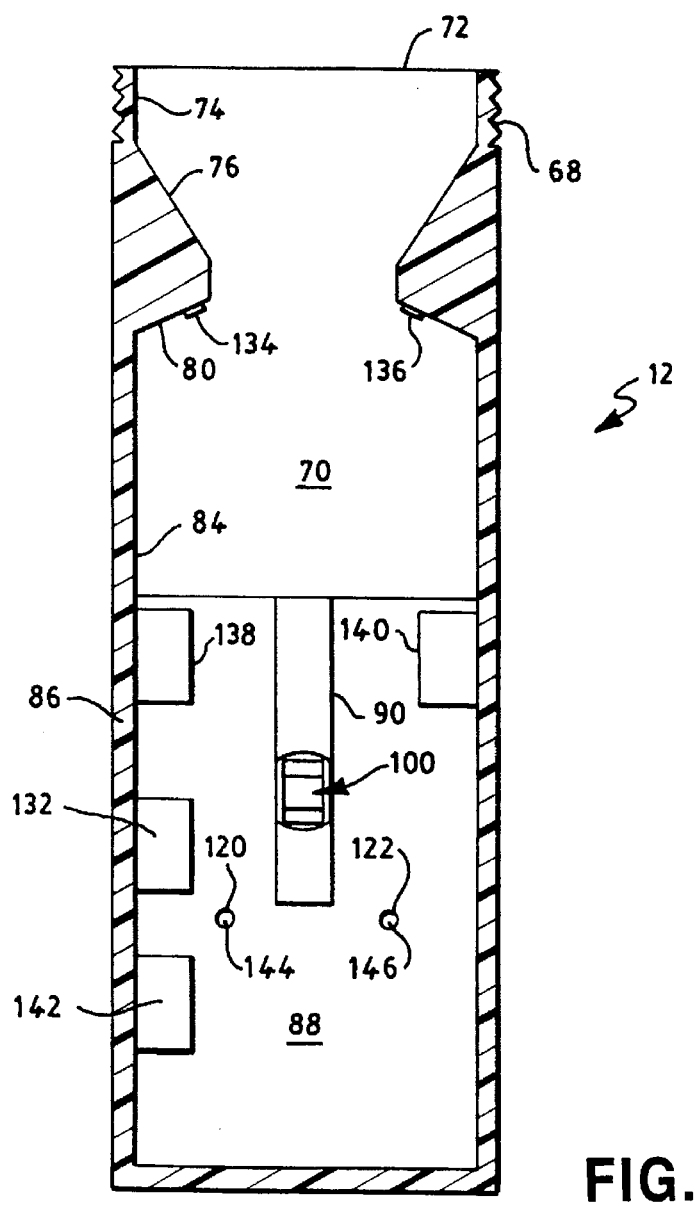
FIG. 3 is a side cross-sectional view of the sheath of FIG. 2 taken along the line 3—3.

FIGS. 2 and 3 show a top view and a side cross-sectional view, respectively, of the sheath 12. Preferably, the sheath 12 is composed of a rigid plastic and is shaped like a cylindrical cup, with a diameter of from 22 to 30 millimeters (mm) and a length of from 80 to 120 mm. In a preferred configuration, 5 mm of the outer surface of the sheath 12 adjacent to the open end 72 is threaded, as at 68. The remainder of the outer surface is approximately smooth. In another configuration, there is a annular protrusion near, but not adjacent to, the open end 72.

The central cavity 70, when viewed from the open end of the sheath 72, as in FIG. 2, is rectangular in shape and the rectangle is centered about the axis of the sheath 12. The narrow dimension of the cavity 70 is from 7 to 8 mm, and the wide dimension is approximately 18 mm at the open end 72 and for a distance of about 5 mm into the sheath 12, as at 74. Extending further into the sheath 12, the wide dimension of the cavity 70 decreases at an angle of about 45° to approximately 12 mm, as at 76, and remains substantially constant for a distance of from 3 to 5 mm, as at 78. The wide dimension increases at an angle of from 70° to 90° to approximately 18 mm, as at 80. The narrowing and widening of the cavity 70 defines a throat 82. The wide dimension of the cavity 70 continues to about 40 mm from the open end 72, as at 84, where the cavity 80 enlarges to a cylindrical shape 88, the thickness of the wall 86 being about 2 mm.

Figure 4:
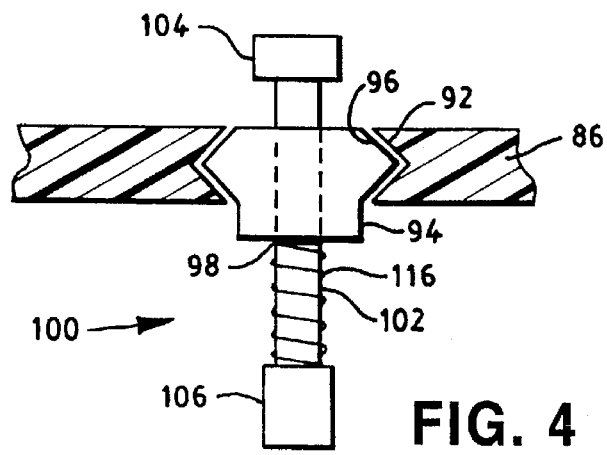
FIG. 4 is a top cross-sectional view of several components of the sheath of FIG. 1.
Figure 5:
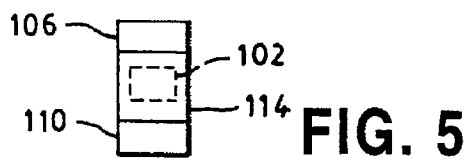
FIG. 5 is an end view of the fork of FIG. 4.

Within the wall 86 is a slot 90 that is 30 to 40 mm long and about 5 mm wide. As shown in FIG. 4, the edges of the slot 92 are formed into a "V" shape and a shuttle 94 with edges 96 adapted to mate with the slot edges 92 fits into the slot 90. Extending through the shuttle 94 and radially to the axis of the sheath 12 is a substantially rectangular bore 98. Located 100. The c rectangular bore 98 is a fork 100. The center portion of the fork 102 has a substantially rectangular cross-section that is substantially the same size as the rectangular bore 98. The center portion 102 combined with the shape of the bore 98, allows the fork 100 to reciprocate radially within the bore 98 but prevents it from rotating within the bore 98. At the end of the center portion 102 outside the sheath 12 is a knob 104 that is large enough so that human fingers can push the fork 100 and shuttle 94 combination lengthwise within the slot 90 and can push and pull the fork 100 into and out of the shuttle bore 98. As in FIG. 5, at the end of the center portion 102 inside the sheath 12, there is a rectangular prong plate 114 perpendicular to the center portion 102. Extending from the upper and lower edges of the prong plate 114, parallel to and away from the center portion 102 are two prongs 106, 110. The length of the prongs 106, 110 is such that, when the fork 100 is pulled out of the shuttle bore 98, the ends of the prongs 106, 110 are not visible when looking from the open end 72 into the cavity 70. Surrounding the center portion 102 is a coil spring 116. The coil spring 116 biases the fork 100 into the sheath 12.

Straddling the slot 90 are two holes 120, 122 in the wall 86. Mounted within these holes 120, 122 are light-emitting diodes (LEDs) 144, 146 for indicating the result of the test performed by the device. The radiating surface of the LEDs faces outside the sheath 12.

Figure 6:
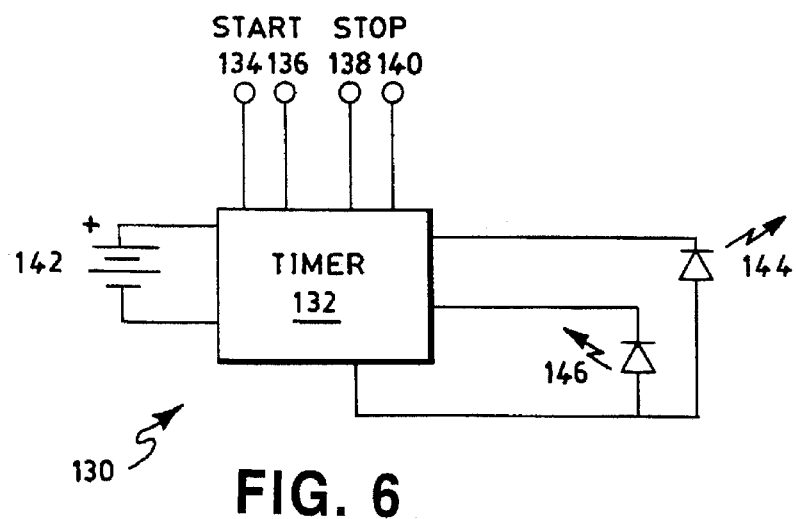
FIG. 6 is an electrical schematic of the timing circuit.

Within the sheath 12 is a timing circuit 130, a schematic diagram of which is shown in FIG. 6. The timing circuit 130 is composed of a timer 132, a pair of start panels 134, 136, a pair of stop panels 138, 140, a battery 142, and the two LEDs 144, 146. When the start panels 134, 136 are electrically connected together, as described below, the timer 132 begins timing. When the stop panels 138, 140 are electrically connected together, as described below, the timer 132 stops timing. The timer 132 then compares the elapsed time to a predetermined value, and if the elapsed time is greater, it energizes one of the LEDs 144 momentarily, otherwise it energizes the other LED 146 momentarily. The battery 142 supplies electrical power to the timing circuit 130.

In an alternative configuration, the timer 132, battery 142, and LEDs 144, 146 are mounted on the outside of the sheath 12 in order to be more easily accessible.

The cap 14 is shaped substantially like an inverted cup that is 60 to 80 mm long and composed of a rigid plastic. In the preferred configuration, the inner surface of the open end 16 is threaded, where the threads are adapted to the outer threads of the sheath 68. In an alternate configuration, there is an annular depression about the inner surface of the open end of the cap that is adapted to mate with the annular protrusion of the sheath. The cap is attached by pressing the cap into the sheath until the protrusion snaps into the depression.

Figure 7:
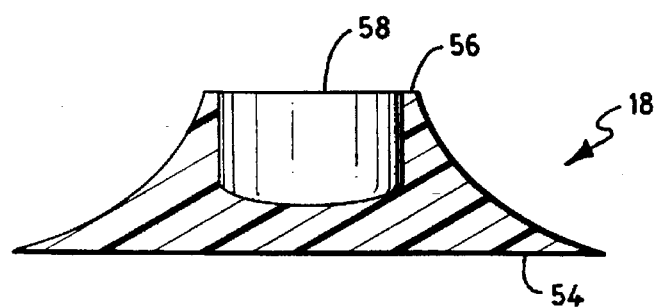
FIG. 7 is a cross-sectional view of the stand of FIG. 1.

The stand 18, shown in cross-section in FIG. 7, holds the sheath 12 in an upright position. In the preferred embodiment, the base of the stand 54 is substantially circular and is about 100 mm in diameter. The side wall slopes upwardly and inwardly to a substantially flat top 56. The top 56 is substantially circular. The height of the stand is approximately 50 mm. Extending about 40 mm into the top 56 is a substantially cylindrical opening 58. The diameter of the opening 58 is substantially the same as the diameter of the sheath 12. The stand 18 is composed of an elastomeric material, such as polyurethane.

Figure 8:
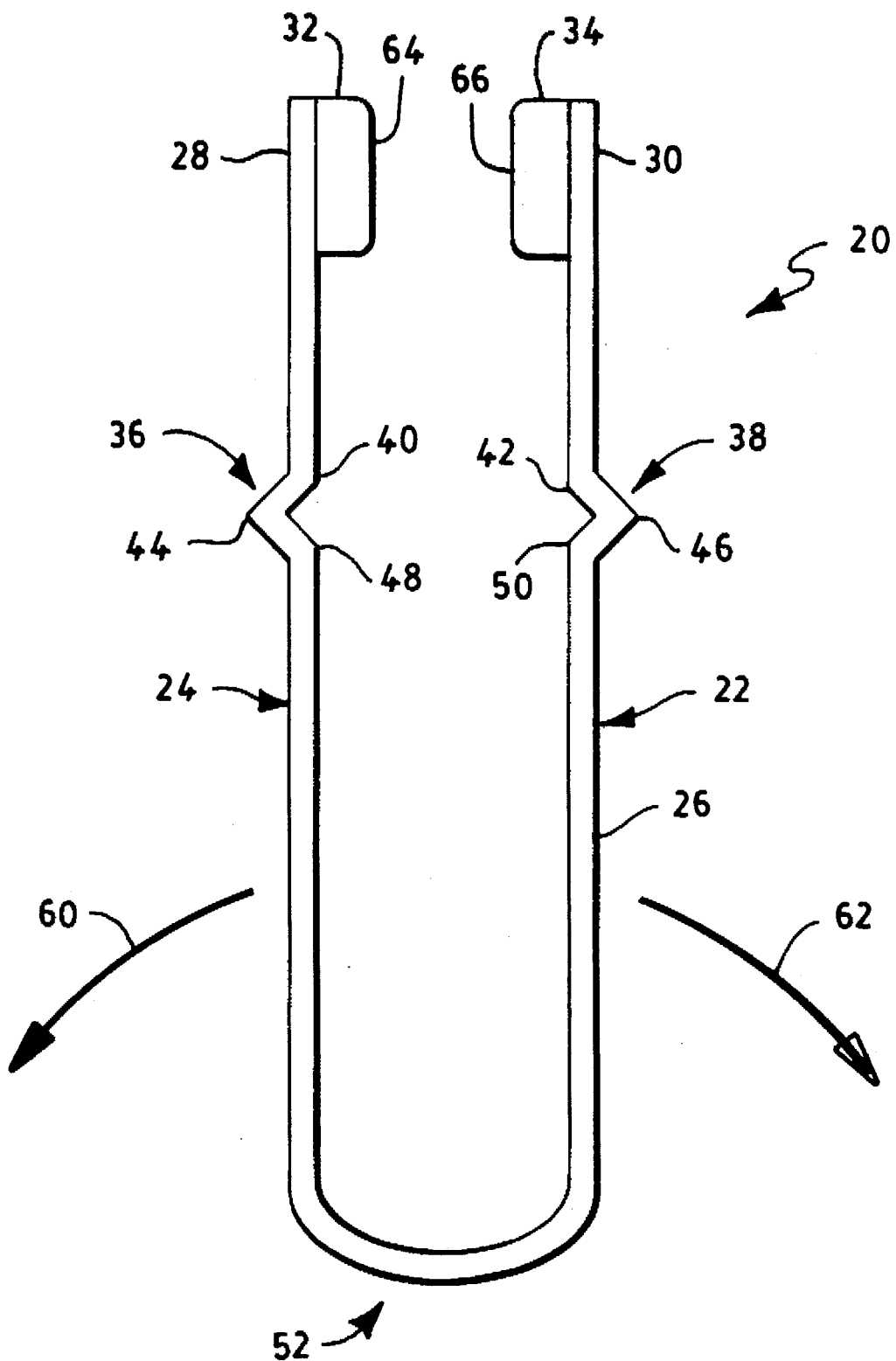
FIG. 8 is a side view of the escapement of FIG. 1.
Figure 9:
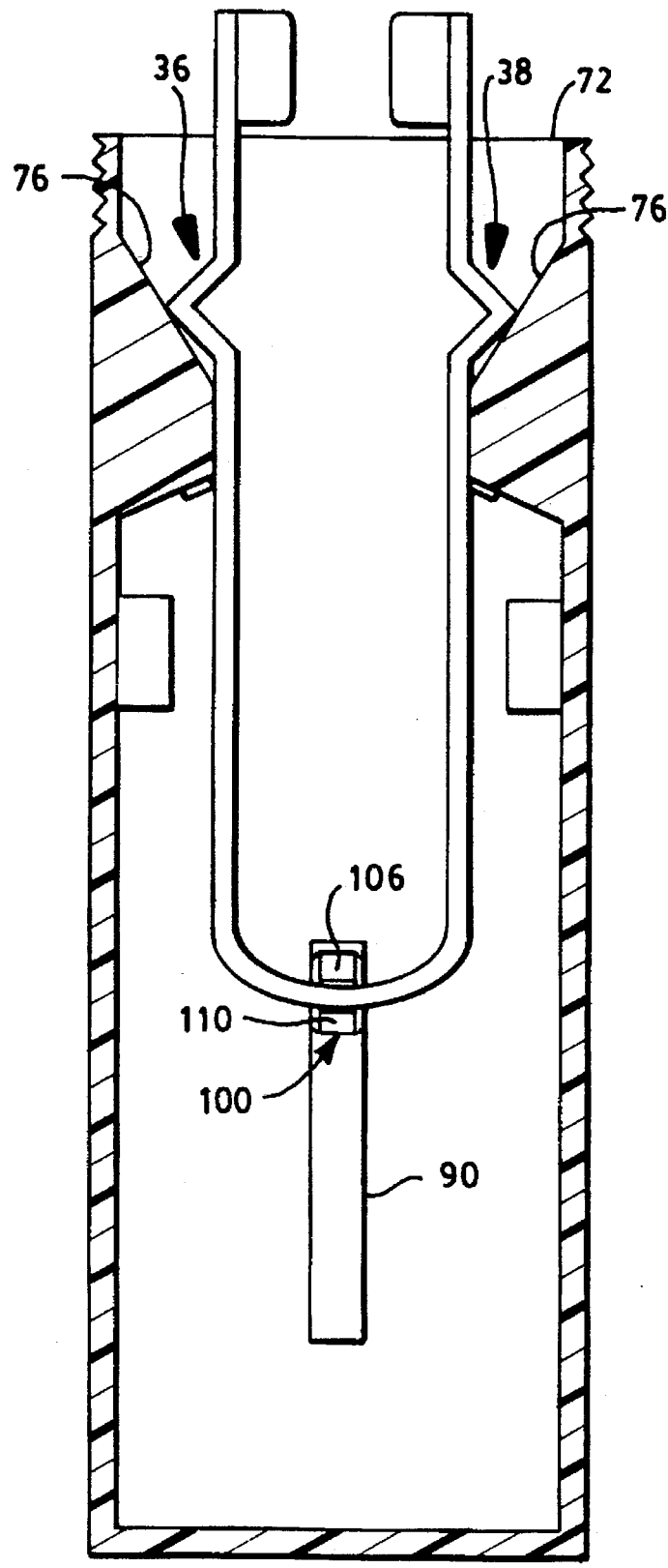
FIG. 9 is a cross-sectional view of the first step of operation of the embodiment of FIG. 1.

As shown in FIG. 8, the escapement 20 is a substantially elongated U-shaped strip of plastic or composite 22 that is coated with an electrically-conductive material. In an alternate configuration, the strip 22 is an electrically-conductive plastic or composite. The strip 22 is from 7 to 8 mm wide and about 2 mm thick. The width prevents the arms 24, 26 of the escapement 20 from twisting longitudinally in normal use. Approximately 35 mm from the outer extremity of each arm 24, 26 is a protrusion 36, 38. The protrusion 36, 38 is created by three bends in the strip 22. The upper bend 40, 42 and the lower bend 48, 50 angle approximately 45° outwardly from the plane of the arm 24, 26, forming the center bend of approximately 90°.

The cross portion of the escapement 20 is at the inner extremities of the arms 22, 24. The curve of the cross portion forms a spring 52, which forces the arms 24, 26 to pivot outwardly from a vertical position to a horizontal position, as at 60, 62. The amount of force exerted by the spring 52 is dependent on the material of which the strip 22 is composed and the thickness of the strip 22. The preferred force is described below.

In one embodiment of the escapement 20, at the outer extremity of each arm 24, 26 is a frame 28, 30 into which are permanently mounted plates 32, 34 by a substantially waterproof adhesive. In a second embodiment, the plates 32, 34 are removably mounted so that the plates 32, 34 may be discarded and replaced. In a third embodiment, the plates are integrally formed with the arms 24, 26. The plates 32, 34 have mating surfaces 64, 66, which are detailed below.

FIGS. 9–12 detail, in cross-section, the internal operation of the dual-prong embodiment 10. Initially, the fork 100 is pushed to the end of the slot 90 nearest the open end of the sheath 72 and then pulled radially out of the sheath 12 by the knob 104 until the fork 100 is stopped by the prong plate 114. Because of the coil spring 116, the fork 100 must be held out of the sheath 12. As in FIG. 9, the escapement 20 is inserted into the open end 72 until the protrusions 36, 38 are resting on the upper throat surface 76. The knob 104 is released so that the coil spring 116 can force the fork 100 back into the sheath 12, after which the upper prong 106 is located just above the spring 52, and the lower prong 110 is located just below the spring 52. In this position, the fork 100 controls the movement of the escapement 20.

Figure 10:
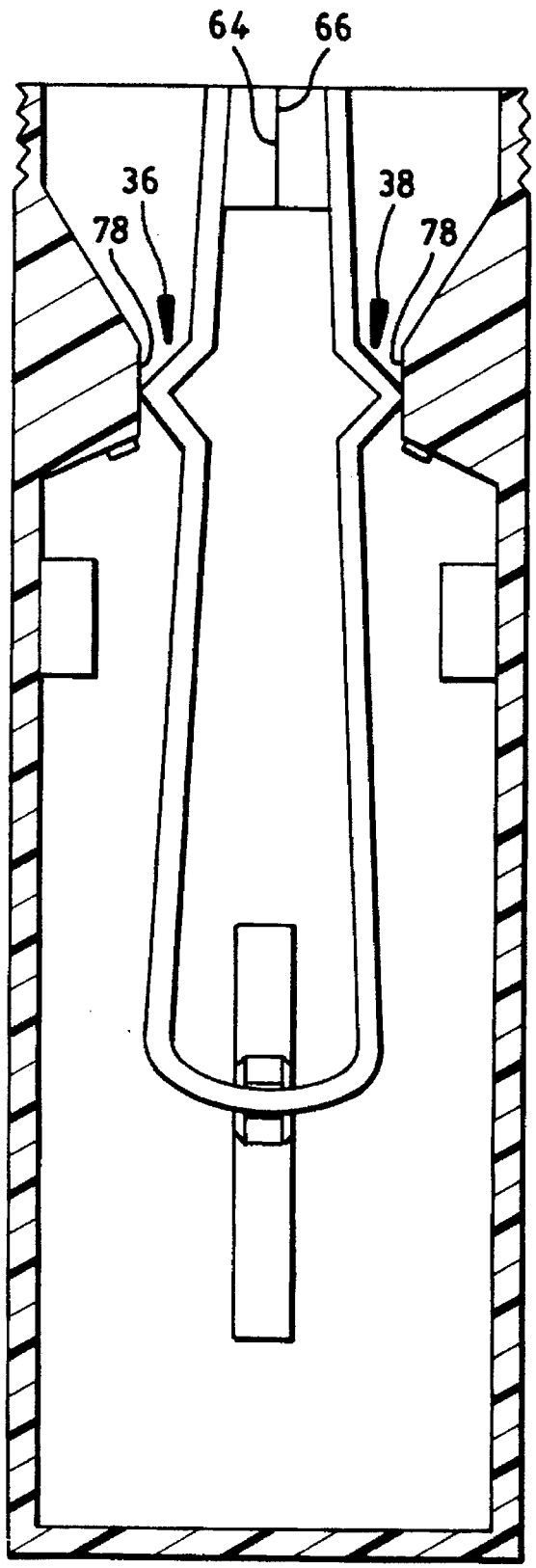
FIG. 10 is a cross-sectional view of the second step of operation of the embodiment of FIG. 1.

In FIG. 10, the operator has pushed the knob 104 away from the open end 72 a short distance. The action of the throat surface 78 on the protrusions 36, 38 is a camming mechanism that causes the mating surfaces 64, 66 to make flush contact. This action causes the upper portions of the escapement legs 22, 24 to deform outwardly at the protrusions 36, 38. The amount of force holding the mating surfaces 64, 66 and, as a consequent, compressing the saliva sample, is related to the amount of protrusion deformation. Preferably, the amount of force between the mating surfaces 64, 66 is approximately 15 grams.

Figure 11:
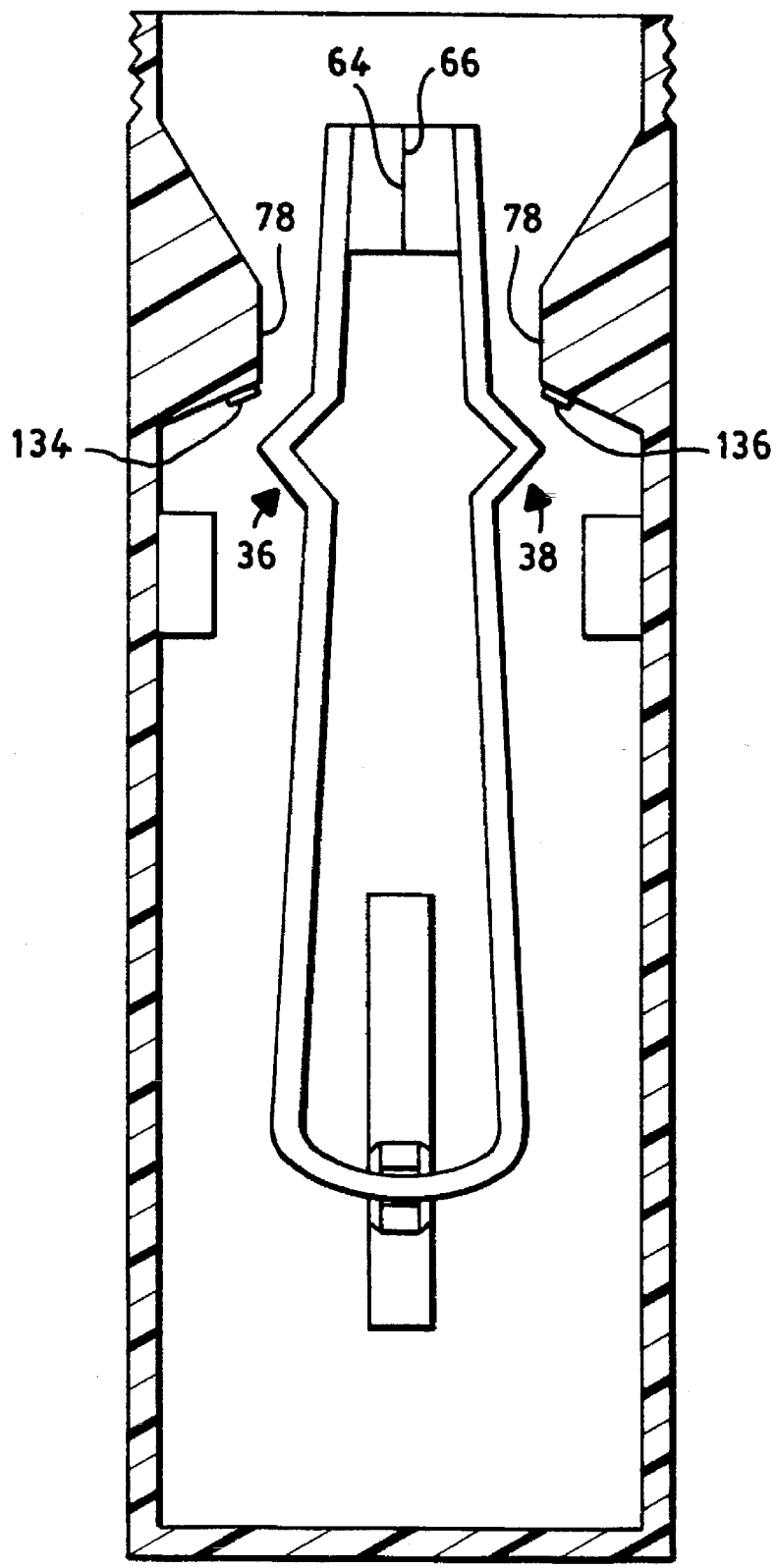
FIG. 11 is a cross-sectional view of the third step of operation of the embodiment of FIG. 1.
Figure 12:
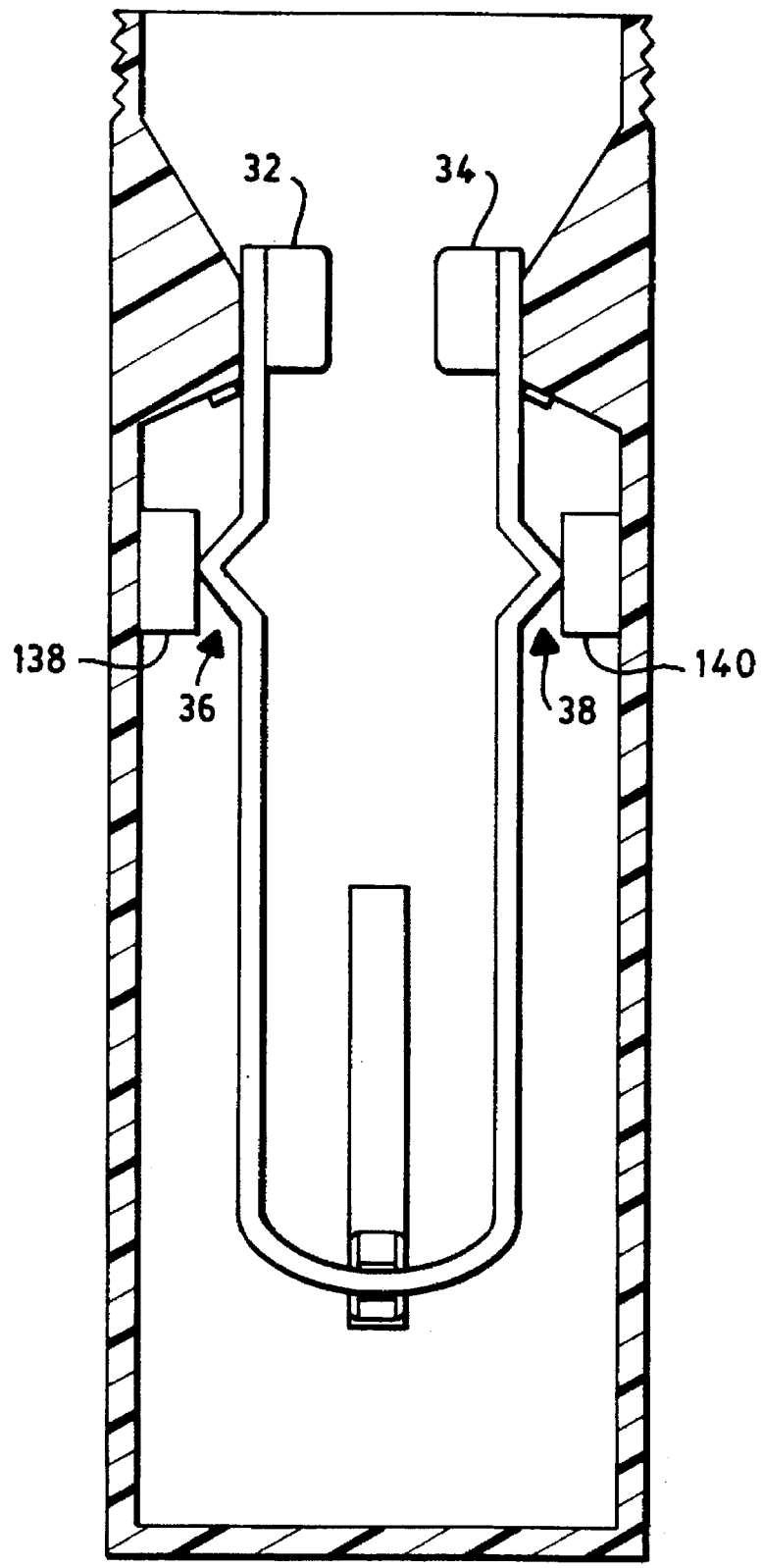
FIG. 12 is a cross-sectional view of the fourth step of operation of the embodiment of FIG. 1.

In FIG. 11, the operator has continued to push the knob 104 from the open end 72. As the protrusions 36, 38 pass the bottom of the throat surface 78, they trigger the timing circuit 130 by electrically connecting the start panels 134, 136. As the escapement 20 continues away from the open end 72, the mating surfaces 64, 66 remain held together by the viscoelasticity of the saliva sample on the mating surfaces 64, 66. In FIG. 12, the escapement 20 has reached the end of its travel. Eventually, the force of the spring 52 overcomes the viscoelasticity of the saliva sample, and the mating surfaces 64, 66 separate. When the mating surfaces 64, 66 separate, the protrusions 36, 38 electrically connect the stop panels 138, 140, signalling the timing circuit 130 to discontinue timing and to indicate the result of the measurement.

The escapement 20 is removable for disposal. To remove the escapement 20, the knob 104 is pushed back to the end of the slot 90 nearest the open end 72. Then the fork 100 is pulled radially out of the sheath 12 by the knob 104, and the escapement 20 is manually removed and disposed of.

Single-Prong Embodiment

Figure 13:
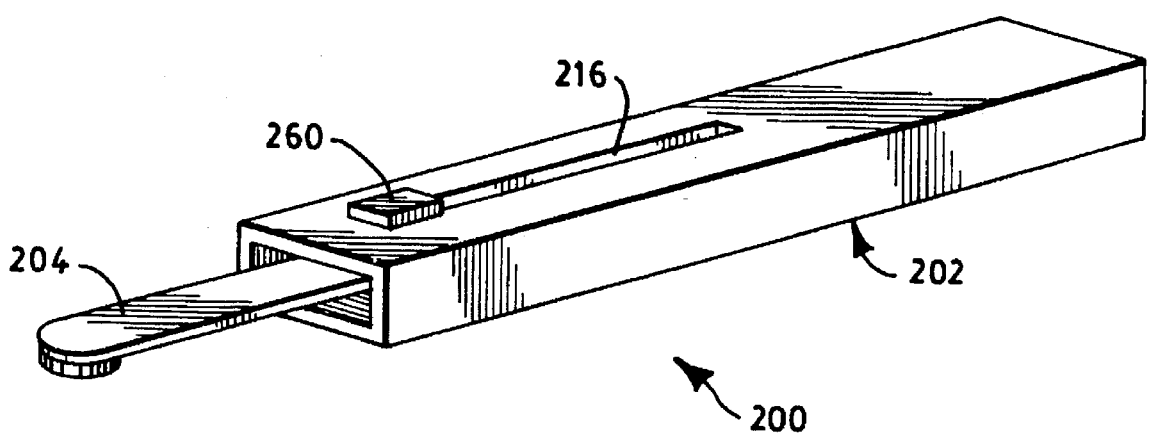
FIG. 13 is a perspective view of a single-prong embodiment of the present invention.

FIG. 13 shows the single-prong embodiment of the present invention 200. In contrast to the first embodiment of FIGS. 1–12, it is a substantially integral construction.

Figure 14:
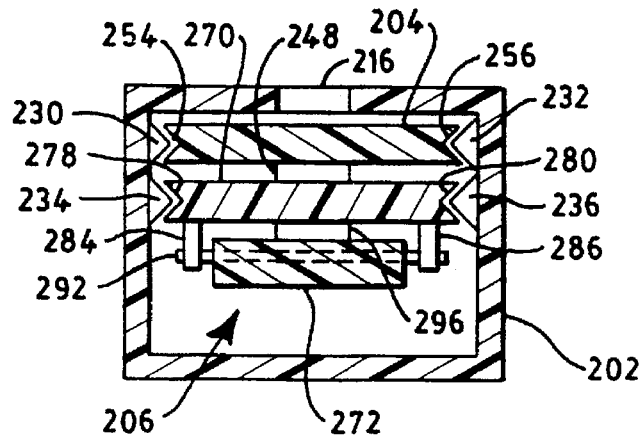
FIG. 14 is a front end cross-sectional view of the embodiment of FIG. 13.
Figure 15:
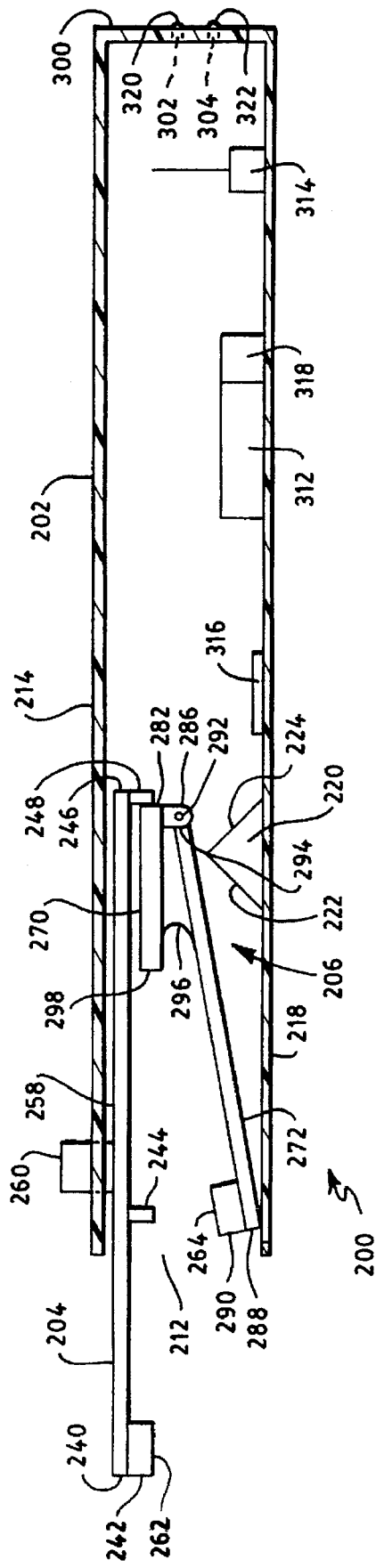
FIG. 15 is a side cross-sectional view of the embodiment of FIG. 13.

FIGS. 14 and 15 show a front cross-sectional view and a side cross-sectional view, respectively. This embodiment 200 has three basic components, the sheath 202, the upper escapement portion 204, and the lower escapement portion 206.

The sheath 202 is composed of a rigid plastic and is approximately rectangular in shape and hollow. It has a height of about 25 mm, a width of about 30 mm, a length of about 130 mm, and a wall thickness of about 2 mm. One end of the sheath has an opening 212 through which the upper escapement portion 204 extends and retracts, as described below. The top wall of the sheath 214 has a longitudinal slot 216 that is approximately 90 mm long and 5 mm wide, the purpose of which is described below. Extending upwardly from the bottom wall 218 is a wedge 220. The leading surface of the wedge 222 slopes at an angle of about 45° to the bottom wall 218 and the trailing surface 224 extends downwardly to the bottom wall 218 away from the opening 212 at an angle of approximately 45°. The wedge 220 has a height of about 10 mm.

Projecting from the two long side walls 226, 228 near to and parallel with the upper wall 214 is a pair of upper rails 230, 232. Below the upper rails 230, 232 is a pair of lower rails 234, 236. In cross-section, all of the rails 230, 232, 234, 236 have a shape like a sideways "V". The purpose of the rails 230, 232, 234, 236 is described below.

Figure 16:
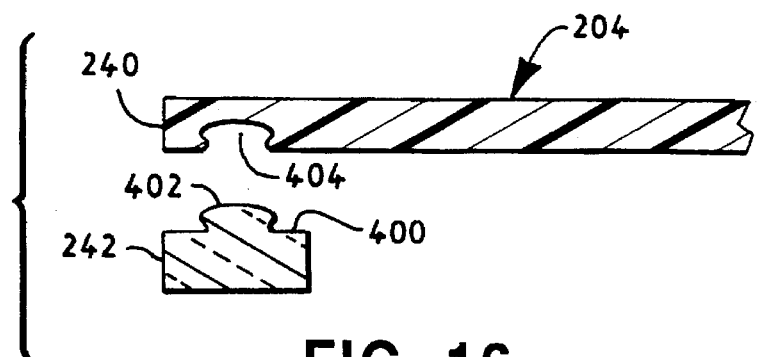
FIG. 16 is a cross-sectional view of a portion of the embodiment of FIG. 13.

The upper escapement portion 204 is a long, thin, rectangularly-shaped solid that is composed of a slightly flexible plastic or composite. It is approximately 75 mm long, 25 mm wide, and 2 mm thick. Attached to the lower surface of the outer extremity of the upper escapement portion 240 is an upper plate 242, which is detailed below. In one embodiment, the upper plate 242 is attached to the upper escapement portion 240 by a substantially waterproof adhesive. In another embodiment, shown in FIG. 16, the upper plate 242 is attached by a snap mechanism. The rear of the upper plate 400 has a cylindrical protrusion 402 where the outer end is slightly larger in diameter than the inner end. In the lower surface of the end of the upper escapement portion 240 is a mating hole 404. The upper plate is attached to the upper escapement portion 204 by pressing the protrusion 402 into the hole 404 until it snaps into place. In a third embodiment, the upper plate 242 is integrally formed with the upper escapement portion 204. The upper plate 242 has a mating surface 262, which is detailed below.

The long edges of the upper escapement portion 204 are adapted by V-shaped indentations 254, 256 to mate with the sheath upper rails 230, 232. The upper rails 230, 232 and the indentations 254, 256 permit the upper escapement portion 204 reciprocate longitudinally within the sheath 202. Extending from the upper surface of the upper escapement portion 258 is a knob 260. The knob 260 is adapted to extend through the slot 216 and provides for manual reciprocation of the upper escapement portion 204 within the sheath 202. Extending downwardly near the center of the upper escapement portion 204 is a push tab 244 and extending downwardly from the inner extremity of the upper escapement portion 246 is a return tab 248. The tabs 244, 248 extend at least below the lower rails 234, 236 when the upper escapement portion 204 is installed on the upper rails 230, 232.

The lower escapement portion 206 has a shuttle 270 and an arm 272. The shuttle 270 is a rectangular solid that is composed of a rigid plastic. It is approximately 25 mm long, 25 mm wide, and 2 mm thick. The long edges of the shuttle 270 are adapted by V-shaped indentations 278, 280 to mate with the sheath lower rails 234, 236. The lower rails 234, 235 and the indentations 278, 280 permit the shuttle 270 reciprocate longitudinally within the sheath 202. When installed in the sheath 202, the shuttle 270 is located between the push tab 244 and return tab 246 of the upper escapement portion 204. Extending downwardly from the rear end of the shuttle 282 and adjacent to the long edges 274, 276 are a pair of ears 284, 286 to which the arm 272 is attached, as described below.

The arm 272 is a long, thin, rectangularly-shaped solid that is composed of a slightly flexible material. It is approximately 50 mm long, 20 mm wide, and 2 mm thick. Attached to the outer extremity of the arm 288 is a lower plate 290. In one embodiment, the lower plate 290 is attached to the arm 272 by a substantially waterproof adhesive. In another embodiment, the lower plate 290 is attached to the arm 272 by a snap mechanism in the same manner as the upper plate 242 described above and in FIG. 16. In a third embodiment, the lower plate 290 is integrally formed with the arm 272. The lower plate 290 has a mating surface 264, which is detailed below. The arm 272 is pivotally attached to the shuttle 270 by an axle 292 that extends through holes in the ears 284, 286 and an edge-to-edge hole through the arm 272 near the inner extremity 294.

Located between the shuttle 270 and the arm 272 is a spring 296. The spring 296 can be a U type spring, as shown in FIG. 14, or a coil-type spring. The spring 296 forces the arm 272 away from the shuttle 270 about the pivot point created by the axle 292.

Located in the rear end of the sheath 300 are two holes 302, 304. Mounted within these holes 302, 304 are two LEDs 320, 322 for indicating the result of the test performed by the device. The radiating surfaces of the LEDs face outside the sheath 202.

Figure 17:
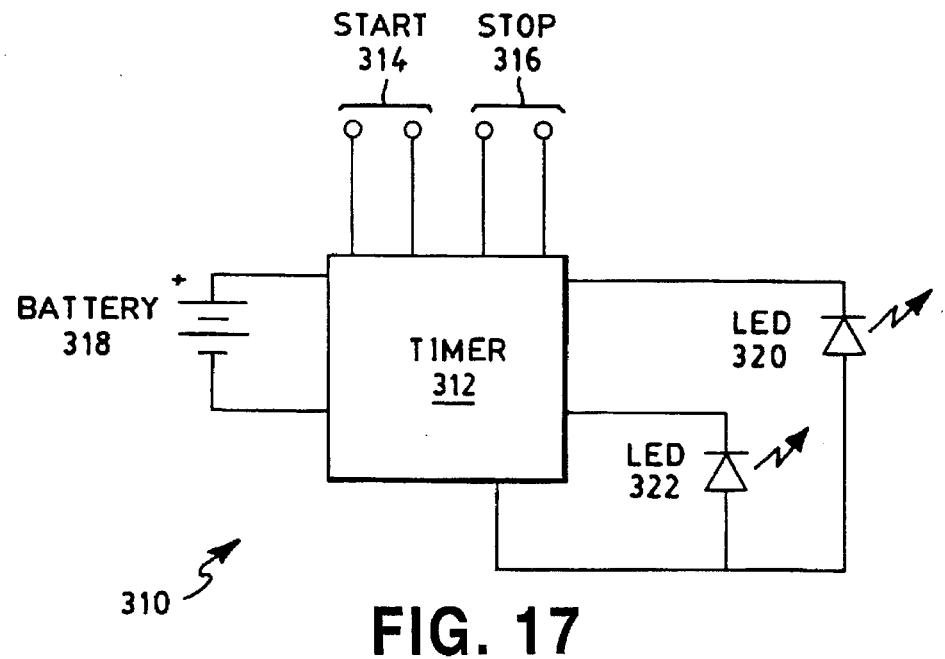
FIG. 17 is an electrical schematic of the timing circuit of the embodiment of FIG. 13.

Within the sheath 202 is a timing circuit 310, a schematic diagram of which is shown in FIG. 17. The timing circuit 310 is composed of a timer 312, a start switch 314, a stop switch 316, a battery 318, and the two LEDs 320, 322. When the start switch 314 is activated as described below, the timer 312 begins timing. When the stop switch 316 is activated as described below, the timer 312 stops timing. The timer 312 then compares the elapsed time to a predetermined value, and if the elapsed time is greater, it energizes one of the LEDs 320 momentarily. Otherwise it energizes the other LED 322 momentarily. The battery 318 supplies electrical power to the timing circuit 310.

In an alternative configuration, the timer 312 and battery 318 are mounted on the outside of the sheath 202 in order to be more easily accessible.

FIGS. 15 and 18–21 detail, in cross-section, the internal operation of the single-prong embodiment 200. Initially, as in FIG. 15, the knob 260 is pushed to the end of the slot 216 nearest the sheath opening 212 so that the upper plate 242 is extending outwardly from the opening 212. Because of the force of the spring 296, the outer extremity end of the arm 288 is in contact with the bottom wall 218.

Figure 18:
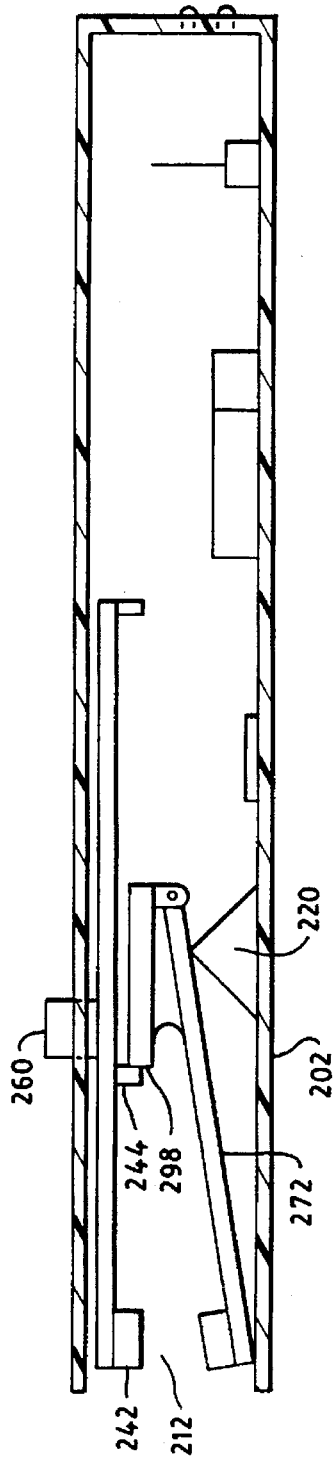
FIG. 18 is a cross-sectional view of the second step of operation of the embodiment of FIG. 13.

As in FIG. 18, the operator has pushed the knob 260 away from the opening 212 a short distance. Pushing the knob 260 causes the upper plate 242 to be withdrawn into the sheath 202 through the opening 212. At the substantially the same moment that the upper plate 242 is completely withdrawn into the sheath 202, the push tab 244 makes contact with the outer extremity of the shuttle 298 and the top edge of the wedge 220 makes contact with the arm 272.

As in FIG. 19, the operator has continued to push the knob 260 away from the opening 212. The push tab 244 is pushing the shuttle 270 along with the upper escapement portion 204. The action of the wedge 220 on the arm 272 acts as a camming mechanism to overcome the force of the spring 296 and cause the arm 272 to pivot upwardly until the mating surfaces 262, 264 make contact. This action causes the upper escapement portion 204 and the arm 272 to deform away from each other. The amount of force holding the mating surfaces 262, 264 and, as a consequence, compressing the saliva sample, is related to the amount of deformation and preferably is approximately 15 grams.

As in FIG. 20, the operator has continued to push the knob 260 away from the opening 212. As the outer extremity of the arm 288 passes the top edge of the wedge 220, the return tab 248 activates the start switch 314 extending from the bottom wall of the sheath 218. The start switch 314 triggers the timer 312. As the upper escapement portion 204 continues rearwardly, the mating surfaces 262, 264 are no longer being forced together by the wedge 220, but remain held together by the viscoelasticity of the saliva sample on the mating surfaces 262, 264. In FIG. 21, the upper escapement portion 204 has reached the end of its travel. Eventually, the force of the spring 296 overcomes the viscoelasticity of the saliva sample, and the mating surfaces 262, 264 separate. When this happens, the outer extremity of the arm 288 stops the timer 312 by activating the stop switch 316 located on the bottom wall 218.

The plates 242, 290 are removable in order to replace them. To remove the plates 242, 290, the knob 260 is pushed back to the end of the slot 216 nearest the opening 212, extending the outer extremity of the upper escapement portion 240 from the opening 212. This allows access to the upper plate 242 for removal. The upper plate 242 is removed by prying it out of the snap hole 404. The lower plate 290 is accessible through the opening 212 and is removed in the same manner as the upper plate 242.

Plates

The plates of both the dual-prong embodiment 10 and single-prong embodiment 200 are substantially the same. Each has a mating surface. When the mating surfaces are in contact, as described above, the area of contact is substantially the entire face area of the plates. Preferably, the plates are approximately round with a face diameter of between 5 and 6.5 mm, which is a face area of approximately 20 to 40 mm$^2$. The plates are between 2 and 5 mm thick.

Figure 22:
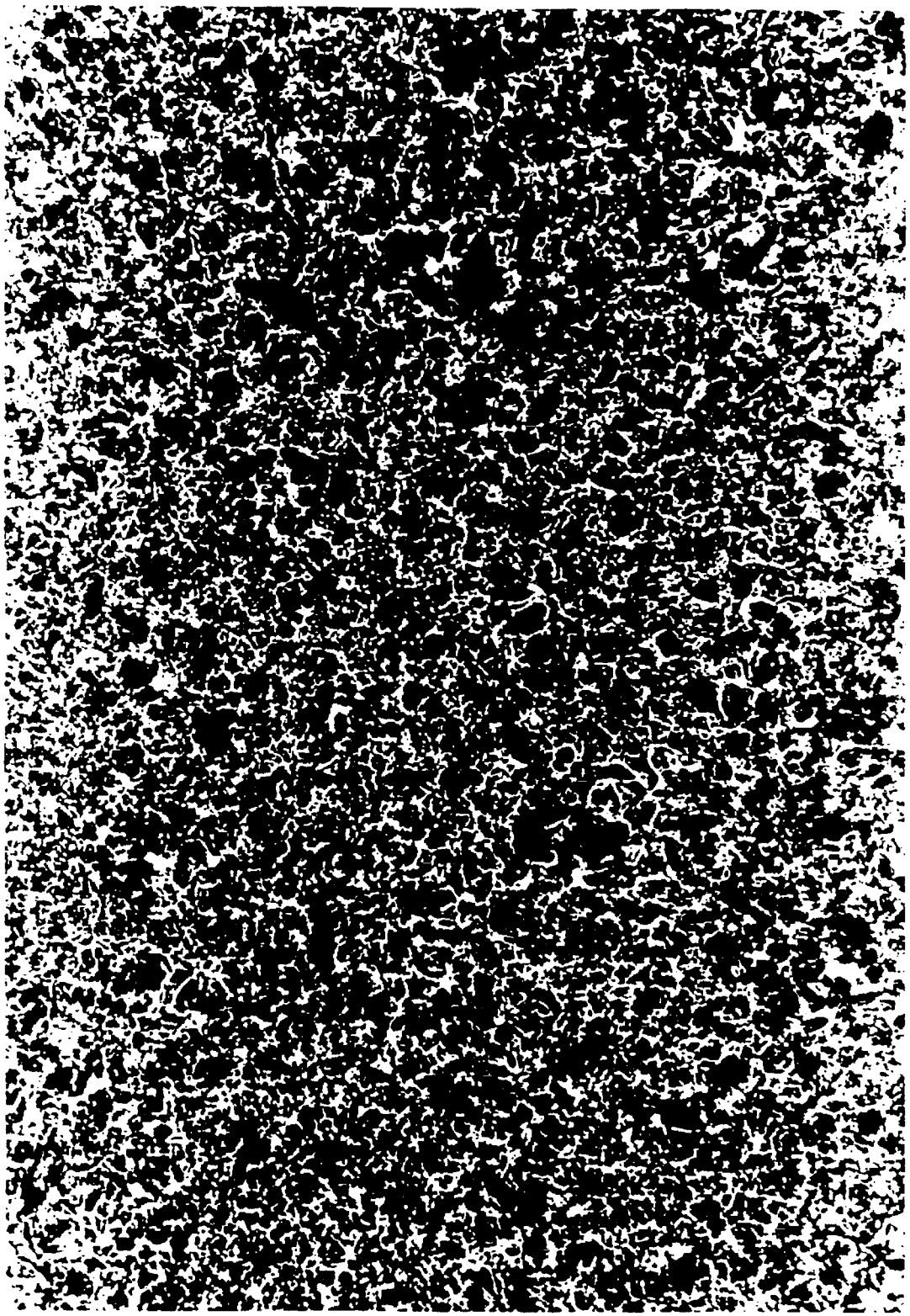
FIG. 22 is a low-power microphotograph of a plate surface.
Figure 23:
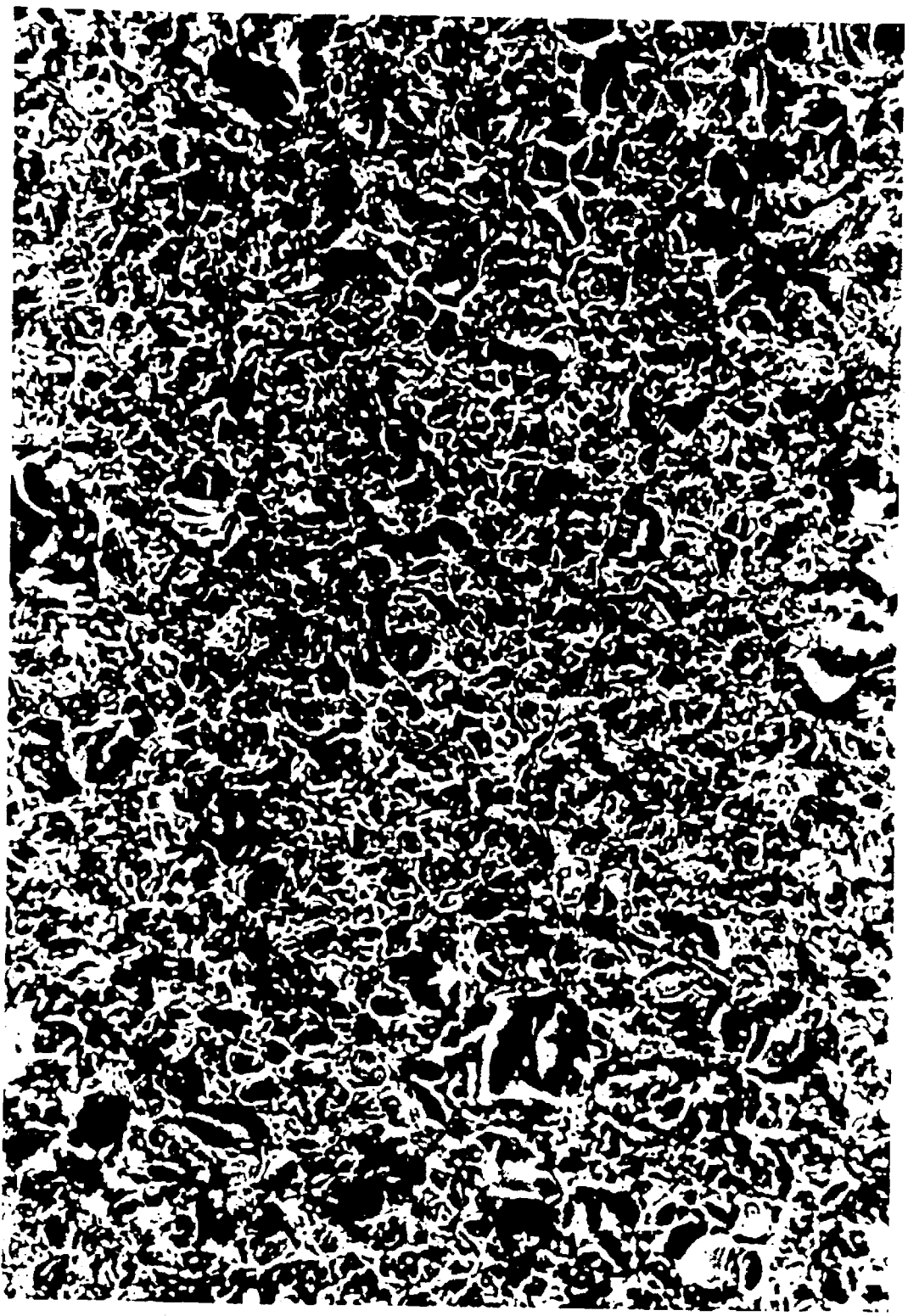
FIG. 23 is a high-power microphotograph of a plate surface.

FIG. 22 is a low-power (10×) microphotograph and FIG. 23 is a high-power (40×) microphotograph of a typical plate surface. As can be seen, the plate surface is rough; it is composed of a random distribution of irregularly shaped valleys and ridges. The height from the floor of a valley to the peak of a ridge is approximately 0.05 to 0.08 mm.

The plates can be composed of glass or a plastic. In the case of glass, the face is ground to above-described roughened surface. In the case of plastic, the surface is etched into the mold from which the plate is formed, eliminating the extra grinding step. In the dual-prong embodiment 10, the plates are preferably composed of plastic, because then the escapement 20 can be molded with the plates as integral components. In the single-prong embodiment 200, the plates are preferably either glass or plastic. Since they are preferably separable from the upper escapement portion 204 and the arm 272 and are not integrally formed with those components, they do not have to composed of the same material as the upper escapement portion 204 and the arm 272.

The plates are intended to be single-use disposable items. The faces can be used for one measurement only because the previous saliva sample will dry in the crevices of the face, causing a subsequent measurement to be invalid since the new saliva sample cannot adhere properly to the face.

Determination of Ovulation Time

The elapsed time measured by the timing circuit 130, 310 is the time it takes for the force of the spring 52, 296 to overcome the tendency of the saliva sample to remain intact. The viscoelasticity of the saliva sample is directly related to this time measurement by the following equation:

$$\text{Viscosity (poise)} = \frac{\text{Shear Stress (grams/centimeter}^2)}{\text{Shear Rate (seconds)}}$$

In the dual-prong embodiment, the preferred size of the plate faces 64, 66 is between about 0.20 and 0.40 cm$^2$. A predetermined constant pressure is applied between the plate faces 64, 66 for a minimum period of time of approximately 2 to 4 seconds when the protrusions 36, 38 are within the throat 82. This pressure compresses and extrudes the saliva sample between the plate faces 64, 66. After the protrusions 36, 38 are beyond the throat 82, the pressure of the spring 52 acts to fracture the saliva sample. The pressure exerted by the spring 52 is approximately from 0.5 to 15 grams, resulting in a shear stress in the range of from 1.25 to 75 g/cm$^2$. The shear stress is divided by the amount of time measured by the timer 130 to arrive at the viscoelasticity of the saliva sample.

In single-prong embodiment, the size of the plate faces 262, 264 is between about 0.20 and 0.40 cm$^2$. A predetermined constant pressure is applied between the plate 262, 264 faces for a minimum period of time of approximately 2 to 4 seconds when the arm 272 is pushed up by the wedge 220. This pressure compresses and extrudes the saliva sample between the plate faces 262, 264. After the front end of the arm 288 is beyond the wedge 220, the pressure of the spring 296 acts to fracture the saliva sample. The pressure exerted by the spring 296 is approximately from 0.5 to 15 grams, resulting in a shear stress in the range of from 1.25 to 75 g/cm$^2$. The shear stress is divided by the amount of time measured by the timer 310 to arrive at the viscoelasticity of the saliva sample.

Figure 24:
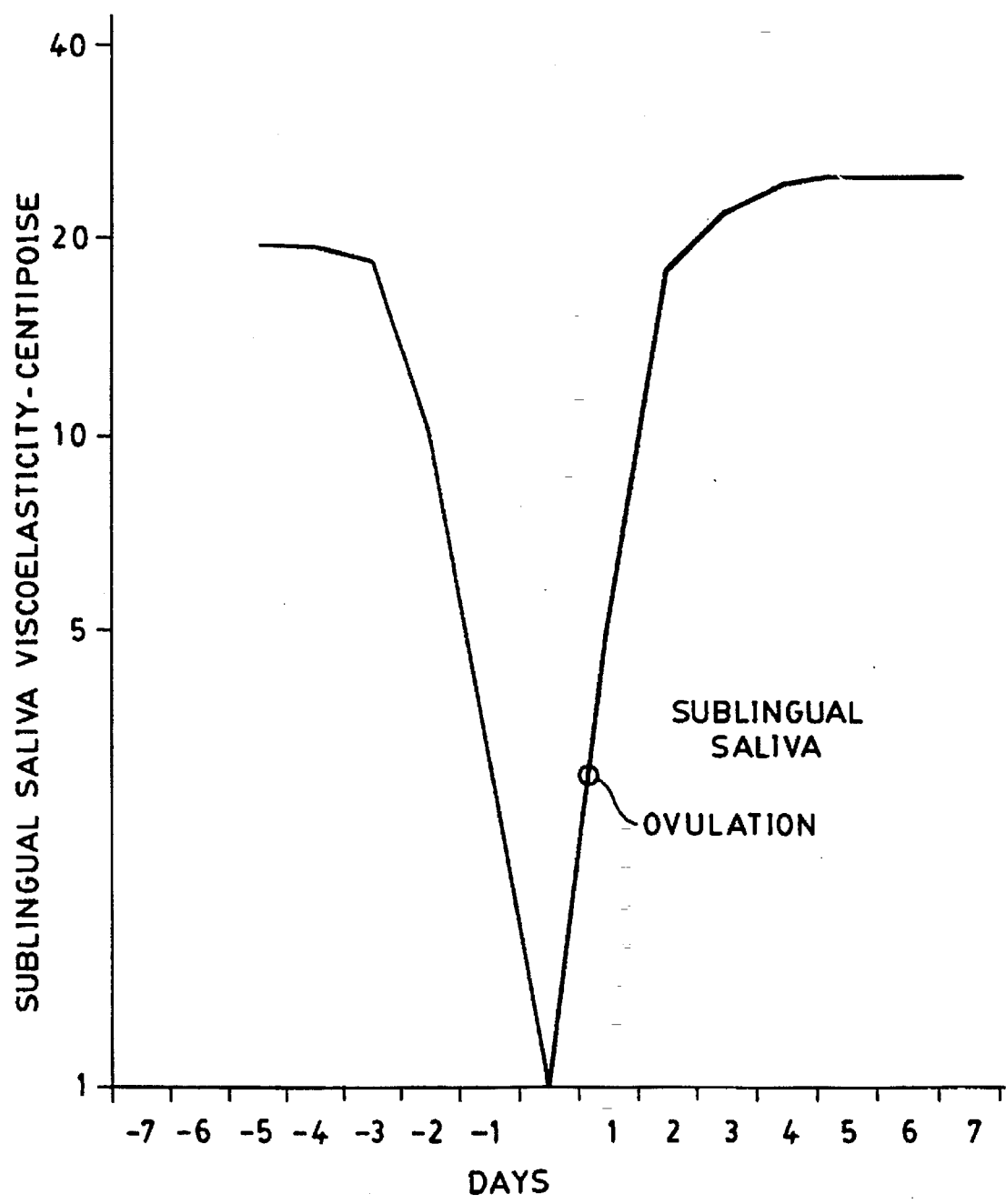
FIG. 24 is a curve showing the relationship between the viscoelasticity of saliva and ovulation time.

The curve of FIG. 24 shows how the viscoelasticity of sublingual saliva relates to the time of ovulation. The viscoelasticity falls over a period of from 2 to 4 days until about 16 to 24 hours prior to ovulation and then rises over a period of from 1 to 2 days.

OPERATION

Each of the two above-disclosed embodiments operate in essentially the same manner. However, there is some variation, so the operation of each is described separately.

Dual-Prong Embodiment

The dual-prong embodiment 10 is designed so that the escapement 20 is disposable. Prior to usage, a new escapement 20 is acquired and inserted into the sheath 12 by the following method: (1) push the knob 104 to the end of the slot 90 near the top end of the sheath 72, (2) pull the knob 104 out of the sheath 12 against the coil spring 116 until it stops and hold the knob 104 out, (3) insert the escapement 20 into the top end 72 until the protrusions 36, 38 are resting on the upper throat surface 76, and (4) release the knob 104, allowing the coil spring 116 to pull the fork 100 back into the sheath 12. During this insertion process, care must be taken to avoid contaminating the plates 32, 34 with any foreign substance, as such contamination will invalidate the measurement.

After the escapement 20 is in place within the sheath 12, the plates 32, 34 are dipped into the mouth in order to retrieve a sample of sublingual saliva from the saliva pool under the tongue. The saliva must cover substantially the entire face of the plates 64, 66. After taking the saliva sample, the bottom end of the sheath 12 is insert into the opening in the stand 18. Then the knob 104 is pushed the full distance of the slot 90 in a substantially smooth motion. If the smooth motion is not maintained or the knob 104 is not pushed the full distance of the slot 90, an invalid measurement will result. After a period of time, one of the LEDs 144, 146 will illuminate momentarily. If one LED 144 illuminates, it is between approximately 48 hours and 5 hours before ovulation. If the other LED 146 illuminates, it is not within that time period before ovulation.

After a measurement is taken, the escapement 20 must be discarded, since it can only be used for one measurement. To remove the escapement 20, push the knob 104 back the full distance of the slot 90, pull the knob 104 out of the sheath 12, and pull the escapement 20 from the sheath 12.

In alternate embodiment, the entire instrument 10 is disposable. In this embodiment, the instrument 10 is acquired with the escapement 20 already installed. After being used for a single measurement, the instrument 10 is disposed of properly.

Single-Prong Embodiment

The single-prong embodiment 200 is designed so that the plates 242, 290 are disposable. Prior to usage, a new pair of plates 242, 290 is acquired and installed onto the outer end of the upper escapement portion 240 and the arm 288 by snapping the upper plate 242 it the hole 404 in the upper escapement portion 204 and by snapping the lower plate 290 in the hole in the arm 272. During this installation process, care must be taken to avoid contaminating the plates 242, 290 with any foreign substance, as such contamination will invalidate the measurement.

After the plates 242, 290 are installed, the upper plate 242 is dipped into the mouth under the tongue in order to retrieve a sample of sublingual saliva. The saliva must cover substantially the entire face of the plate 262. After taking the saliva sample, the knob 260 is pushed the full distance of the slot 216 in a substantially smooth motion. If the smooth motion is not maintained or the knob 260 is not pushed the full distance of the slot 216, an invalid measurement will result. After a period of time, one of the LEDs 320, 322 will illuminate momentarily. If one LED 320 illuminates, it is between approximately 48 hours and 5 hours before ovulation. If the other LED 322 illuminates, it is not within that time period before ovulation.

After a measurement is taken, the plates 242, 290 must be discarded, since it can only be used for one measurement. To remove the plates 242, 290, push the knob 260 back the full distance of the slot 216 and pry the upper plate 242 from the hole 404. Remove the lower plate 290 by prying it from the arm hole.

In alternate embodiment, the entire instrument 200 is disposable. In this embodiment, the instrument 10 is acquired with the plates 242, 290 already installed. After being used for a single measurement, the instrument 200 is disposed of properly.

What is claimed is:

1. A device for determining the timing of female ovulation by measuring the viscoelasticity of saliva, said device comprising:
   (a) an elongated sheath having a length along an axis and an opening at one extremity;
   (b) a reciprocable escapement including a pair of elongated arms, at least one of said arms being disposed approximately parallel to said axis, said arms having inner extremities within said sheath remote from said opening and outer extremities in the vicinity of said opening;
   (c) said outer extremities having mating surfaces;
   (d) said escapement including a spring bias urging the separation of said mating surfaces from each other;
   (e) said arms being mounted for relative movement of said mating surfaces among first relational positions at which said mating surfaces are separated, second relational positions at which said mating surfaces are in contact, and third relational positions at which said mating surfaces are free to separate under said spring bias;
   (f) a control operatively connected to said escapement for optionally placing said mating surfaces into said first relational positions, said second relational positions, and said third relational positions;
   (g) at least one of said mating surfaces being free to collect said saliva when said mating surfaces are in said first relational positions;
   (h) said mating surfaces being constrained to compress said saliva therebetween when said mating surfaces are in said second relational positions; and
   (i) a timer for measuring the time elapsed for separation of said surfaces when said surfaces are in said third relational positions.

2. The device of claim 1 wherein said saliva is sublingual.

3. The device of claim 1 wherein said escapement is removable for disposal and replacement.

4. The device of claim 1 wherein both of said arms are disposed substantially parallel to said axis.

5. The device of claim 1 wherein each of said outer extremities includes a plate, said mating surface being on said plate.

6. The device of claim 5 wherein said plates are permanently mounted.

7. The device of claim 5 wherein said plates are removably mounted.

8. The device of claim 1 wherein said mating surfaces are adapted to retain said saliva in a manner that causes said saliva to internally fracture before said saliva overcomes its adhesion to said mating surfaces.

9. The device of claim 1 wherein said spring bias includes a junction at said inner extremities of said escapement.

10. The device of claim 1 wherein said control includes a camming mechanism for moving said mating surfaces from said first relational position into said second relational positions and from said second relational positions to said third relational positions.

11. The device of claim 10 wherein said camming mechanism includes opposing protrusions on said arms, a throat within said sheath aligned with said axis, and a knob outside said sheath for moving said escapement linearly along said length through said throat, whereby the movement of said protrusions into said throat causes said mating surfaces to move from said first relational positions to said second relational positions and the movement of said protrusions out of said throat causes said mating surfaces to move from said second relational positions to said third relational positions.

12. The device of claim 1 wherein said timer is electronic.

13. The device of claim 1 wherein said timer includes a visual indicator.

14. A device for determining the timing of female ovulation by measuring the viscoelasticity of sublingual saliva, said device comprising:
   (a) an elongated sheath having a length along an axis and an opening at one extremity;
   (b) a reciprocable escapement including a pair of elongated arms, at least one of said arms being disposed approximately parallel to said axis, said arms having inner extremities within said sheath remote from said opening and outer extremities in the vicinity of said opening;
   (c) said outer extremities having mating surfaces, said mating surfaces being adapted to retain said sublingual saliva in a manner that causes said saliva to internally fracture before said saliva overcomes its adhesion to said mating surfaces;
   (d) said escapement including a spring bias urging the separation of said mating surfaces from each other;
   (e) said arms being mounted for relative movement of said mating surfaces among first relational positions at which said mating surfaces are separated, second relational positions at which said mating surfaces are in contact, and third relational positions at which said mating surfaces are free to separate under said spring bias;
   (f) a control operatively connected to said escapement for optionally placing said mating surfaces into said first relational positions, said second relational positions, and said third relational positions, said control including a camming mechanism for moving said mating surfaces from said first relational position into said second relational positions and from said second relational positions to said third relational positions;
   (g) at least one of said mating surfaces being free to collect said sublingual saliva when said mating surfaces are in said first relational positions;
   (h) said mating surfaces being constrained to compress said sublingual saliva therebetween when said mating surfaces are in said second relational positions; and
   (i) an electronic timer for measuring the time elapsed for separation of said surfaces when said surfaces are in said third relational positions, said timer including a visual indicator.

15. The device of claim 14 wherein said escapement is removable for disposal and replacement.

16. The device of claim 14 wherein both of said arms are disposed substantially parallel to said axis.

17. The device of claim 14 wherein each of said outer extremities includes a plate, said mating surface being on said plate.

18. The device of claim 17 wherein said plates are removably mounted.

19. The device of claim 17 wherein said plates are permanently mounted.

20. The device of claim 14 wherein said spring bias includes a junction at said inner extremities of said escapement.

21. The device of claim 14 wherein said camming mechanism includes opposing protrusions on said arms, a throat within said sheath aligned with said axis, and a knob outside said sheath for moving said escapement linearly along said length through said throat, whereby the movement of said protrusions into said throat causes said mating surfaces to move from said first relational positions to said second relational positions and the movement of said protrusions out of said throat causes said mating surfaces to move from said second relational positions to said third relational positions.

22. A device for determining the timing of female ovulation by measuring the viscoelasticity of sublingual saliva, said device comprising:
   (a) an elongated sheath having a length along an axis and an opening at one extremity;
   (b) a reciprocable escapement including a pair of elongated arms, said arms being disposed approximately parallel to said axis, said arms having inner extremities within said sheath remote from said opening and outer extremities in the vicinity of said opening;
   (c) said outer extremities having mating surfaces, said mating surfaces being adapted to retain said sublingual saliva in a manner that causes said saliva to internally fracture before said saliva overcomes its adhesion to said mating surfaces;
   (d) said escapement including a junction at said inner extremities, said junction including a spring bias urging the separation of said mating surfaces from each other;
   (e) said arms being mounted for relative movement of said mating surfaces among first relational positions at which said mating surfaces are separated, second relational positions at which said mating surfaces are in contact, and third relational positions at which said mating surfaces are free to separate under said spring bias;
   (f) a control operatively connected to said escapement for optionally placing said mating surfaces into said first relational positions, said second relational positions, and said third relational positions, said control including a camming mechanism for moving said mating surfaces from said first relational position into said second relational positions and from said second relational positions to said third relational positions;
   (g) said camming mechanism including opposing protrusions on said arms, a throat within said sheath aligned with said axis, and a knob outside said sheath for moving said escapement linearly along said length through said throat, whereby the movement of said protrusions into said throat causes said mating surfaces to move from said first relational positions to said second relational positions and the movement of said protrusions out of said throat causes said mating surfaces to move from said second relational positions to said third relational positions;
   (h) at least one of said mating surfaces being free to collect said sublingual saliva when said mating surfaces are in said first relational positions;

(i) said mating surfaces being constrained to compress said sublingual saliva therebetween when said mating surfaces are in said second relational positions; and (j) an electronic timer for measuring the time elapsed for separation of said surfaces when said surfaces are in said third relational positions, said timer including a visual indicator.

23. The device of claim 22 wherein said escapement is removable for disposal and replacement.

24. The device of claim 22 wherein each of said outer extremities includes a plate, said mating surface being on said plate.

25. The device of claim 24 wherein said plates are removably mounted.

26. The device of claim 24 wherein said plates are permanently mounted.

* * * * *